United States Patent
Tse et al.

(10) Patent No.: US 6,871,526 B2
(45) Date of Patent: Mar. 29, 2005

(54) APPARATUS AND METHOD FOR HEAT TESTING CANISTERS

(75) Inventors: Pius H. Tse, Denville, NJ (US); Mahesh G. Kulkarni, Bridgewater, NJ (US); John M. Jew, Long Valley, NJ (US)

(73) Assignee: Schering Corporation, Kenilworth, NJ (US)

(*) Notice: Subject to any disclaimer, the term of this patent is extended or adjusted under 35 U.S.C. 154(b) by 334 days.

(21) Appl. No.: 10/265,831

(22) Filed: Oct. 7, 2002

(65) Prior Publication Data
US 2003/0121327 A1 Jul. 3, 2003

Related U.S. Application Data
(60) Provisional application No. 60/327,985, filed on Oct. 9, 2001.

(51) Int. Cl.[7] .................................................. G01M 3/00
(52) U.S. Cl. .......................................................... 73/52
(58) Field of Search ...................... 73/52, 432.1, 865.8, 73/865.9; 374/45, 54, 55, 57

(56) References Cited

U.S. PATENT DOCUMENTS

| | | |
|---|---|---|
| 2,915,895 A | 12/1959 | Neiss |
| 3,091,958 A | 6/1963 | Robins |
| 3,460,125 A | 8/1969 | Liebermann et al. |
| 3,852,995 A | 12/1974 | Duncanson ................ 73/40 |
| 3,872,714 A | 3/1975 | Carlson, Jr. .............. 73/46 |

*Primary Examiner*—Robert Raevis
(74) *Attorney, Agent, or Firm*—James M. Gould

(57) ABSTRACT

An apparatus for heat stress testing canisters having bodies and valve assemblies, including a heating zone, such as an induction coil system for heating the canisters, and a conveying assembly for conveying the longitudinal axis of each canister in a generally vertical orientation relative to the longitudinal axis of the heating zone, the canisters being positioned partially within the heating zone during the heat testing, such that, each canister's body is positioned substantially inside of the heating zone and each canister's valve assembly is positioned substantially or completely outside of the heating zone.

41 Claims, 6 Drawing Sheets

APPARATUS AND METHOD FOR HEAT TESTING CANISTERS

CROSS-REFERENCE TO RELATED APPLICATIONS

This application is a non-provisional application that claims priority under 35 U.S.C. § 119(e) of provisional application, U.S. Ser. No. 60/327,985 filed Oct. 9, 2001, the contents of which are hereby incorporated by reference in their entireties.

BACKGROUND OF THE INVENTION

1. Field of the Invention

The invention relates to an apparatus and method for heat stress testing canisters.

2. Description of Related Art

The U.S. Food and Drug Administration has requested that medical inhalation aerosol canister products be subjected to heat stress testing. Further, the Department of Transportation has required for any product or container having more than four ounces of propellant to undergo similar heat stress testing.

Inhalation aerosol canisters may be used to contain and administer a variety of pharmaceutical drugs. For example, these types of devices have been used to contain a bronchodilator and one or more propellants, such as Proventil® (Schering Corporation, Kenilworth, N.J.), which contains albuterol (active ingredient) and a combination of trichloromonofluoromethane and dichlorodifluoromethane (propellants).

The effects of thermal and mechanical stressing on canisters have been studied to ensure that the product could withstand recommended maximum storage temperatures (e.g., for Proventil® canisters, 49° C./120° F.-112 psig). Heat stress testing can be performed as a check on the (crimp) integrity of the canister valve. Heat stress testing can be accomplished via a variety of ways, for instance, by using a (a) water bath heater, (b) conductive heat block conveyor, (c) mechanical vacuum, (d) induction heater, (e) microwave heater, (f) infrared heat gun, (g) laser, and the like.

An induction heater (heat tunnel) utilizes radio frequencies to generate heat within conductive materials (e.g., metals, polymers, etc), such as a metal canister, where resistive heating within the metal of the canister heats the internal contents of the canister and causes thermal stressing therein. The efficacy of a canister can be tested by applying thermal stress to it. Applying heat stress to a canister increases the pressure within the canister, which can accelerate the loss of propellant(s) from grossly leaking canisters with seriously faulty crimps. It has been found, however, that the value of conventional testing is limited because the testing itself could cause damage to the valves of the canisters.

Referring to the figures, a diagram of a prior art, induction heat tunnel stress testing apparatus is shown in FIG. 1. An induction heat tunnel 100 includes an induction coil system 102 powered by a power supply 104. For example, the induction coil system 102 can be a fourteen inch copper induction heating coil, and the power supply can be a 7.5 kW DC power supply. The induction heat tunnel 100 can be used to conduct heat stress testing on a representative number of metal canisters 106 from each manufacturing batch (e.g., 10% of the batch) by raising internal pressures of the canisters 106 to desired levels, for example, about 80–90 psi (34–39° C.).

As shown in FIG. 1, the canisters 106 are conveyed through the induction heat tunnel 100 so that a longitudinal axis of the canister is in a substantially horizontal position relative to a longitudinal axis of a heating zone of the induction coil system 102. The required heat stress is achieved by adjusting the conveyor speed and the power input to the induction coil system 102. The canisters 106 are completely enclosed by and uniformly heated within the induction coil system 102, which emits electromagnetic waves to heat stress the canisters 106. The application of heat radiation can increase the internal pressure in each canister 106. This increase in pressure, caused by the thermal stress, can accelerate the loss of propellants from grossly leaking canisters with faulty crimps.

Referring again to the figures, FIG. 2 is a prior art, partial cross-sectional view of a typical, normally functional metered dose valve 10, which when actuated provides an exact defined amount of drug product to the patient, with FIG. 3 being a top plan view thereof. FIG. 4 shows an enlarged cross-sectional view of the circled portion of the valve 10 of FIG. 2. As shown therein, the valve 10 includes an annular valve body 12 with an annular projection 14. The valve body 12 is that portion of the valve 10 that provides the metered dose of drug to the patient. An annular rubber valve seat 16 sits on the annular projection 14 and provides a seal with a valve stem 18 positioned axially within the valve body 12 and the valve seat 16. The valve seat 16 is a rubber seat located at the base of the valve stem 18 and at the center of the valve body 12, and provides a seal between the valve body 12 and the valve stem 18. As shown in FIG. 3, during normal functioning of the valve 10, the inner surface of the valve seat 16 provides a seal against the outer surface of the valve stem 18.

However, as a result of thermal stress testing, the rubber valve seat 16 can become deformed around the valve stem 18, which deformation is shown in exaggerated form in FIGS. 5 (top plan view) and 6 (enlarged cross-sectional view). In the state shown in FIG. 6, the valve seat 16 forms a so-called "dog ear" deformation 17, which is a severe deformation of the rubber valve seat 16 in the shape of a dog's ear.

Furthermore, as a result of the increased heat applied to the canister (and the increased pressure generated within the canister) during thermal stress testing, the rubber valve seat 16 of the canister occasionally deforms, whereby a condition known as "blow-by" occurs. "Blow-by", as used herein with respect to a canister, is defined as a defect classified by an irregular or continuous spray (or discharge) upon actuation of the valve 10 and/or the presence of a residue from a product that has leaked out between the valve stem 18 and the valve seat 16 (or a gasket) onto metal valve ferrule components 22 of the canister. The valve ferrule 22 is an aluminum portion of the valve 10 that holds the rubber valve seat 16 in place at the base of the valve stem 18. "Blow-by" can result from the deformation of the rubber valve seat 16 around the valve stem 18, which produces a gap at a corner of the metal valve ferrule 22. "Blow-by" can sometimes be heard as a "hollow" sound produced on actuation of the valve 10 and can also be accompanied by an irregular continuous spray (or discharge). Canisters that have been thermally stressed so as to produce "blow-by" were x-rayed imaged and often shown to have a large gap 20 at the corner of the valve ferrule 22, which was produced by the deformation of the valve seat 16.

Accordingly, this method of heat stress testing can result in the damage and/or destruction of the canister valve or other components of the canister. Thus, there is a need for an adequate in-process heat stress testing apparatus and method that does not damage the canister contents or valve components in order to ensure canister integrity and, thus, product quality for patients. It would be desirable to provide an apparatus and method for heat stress testing canisters that do not damage and/or destroy valve and/or other components of the canisters.

SUMMARY OF THE INVENTION

In accordance with the present invention, apparatuses are provided for heat (stress) testing canisters that comprise a body and a valve assembly. The present invention further provides methods of using such apparatuses to test the canisters. The canisters that have been tested by the methods of the present invention are also provided by the present invention. Preferably, such canisters contain a pharmaceutical drug.

One embodiment of the present invention is an apparatus and corresponding method of use thereof, that comprises a heating assembly comprising a heating zone for heating at least a portion of the canister, and a conveying assembly that conveys the canister in an orientation that positions the canister partially within the heating zone of the heating assembly during heat testing. In this manner, the canister body is positioned substantially inside the heating zone, while the canister valve assembly is positioned substantially outside of the heating zone.

In this embodiment, when the heating zone is being heated, only the canister body positioned substantially therein will be exposed to heat radiation, thus, leaving the canister valve assembly unaffected by the heat stress testing. This embodiment is easily adapted for use in a production line for testing a manufacturing batch (or lot)) of canisters.

The above and other features of the invention will become readily apparent from the following detailed description thereof, which is to be read in connection with the accompanying drawings.

DETAILED DESCRIPTION

By "substantially" positioning the canister body "inside" the heating zone, it is meant that greater than about 50%, preferably, greater than about 75%, more preferably, greater than about 90%, and most preferably, greater than about 95%, of the canister body is situated within the heating zone for exposure to heat radiation.

By "substantially" positioning the canister valve assembly "outside" the heating zone, it is meant that greater than about 90%, preferably, greater than about 95%, more preferably, greater than about 99%, and most preferably, all of the canister valve assembly is situated outside of the heating zone so that it will be exposed to little or, preferably, no heat radiation when the heating zone is being heated.

Many conventional heating (and conveying) assemblies operate in a substantially horizontal direction, that is, a longitudinal (central) axis of each canister is substantially horizontal, relative to a longitudinal axis of a heating zone of the heating assembly, when the canister moves through the heating zone. "Substantially horizontal", as used herein with respect to the orientation of a canister, means the canister is positioned more horizontally than vertically (e.g., about <45° or about >135° deviation from the respective horizontal axis), and includes a completely horizontal position, as illustrated in prior art FIG. 1.

Figure 7:
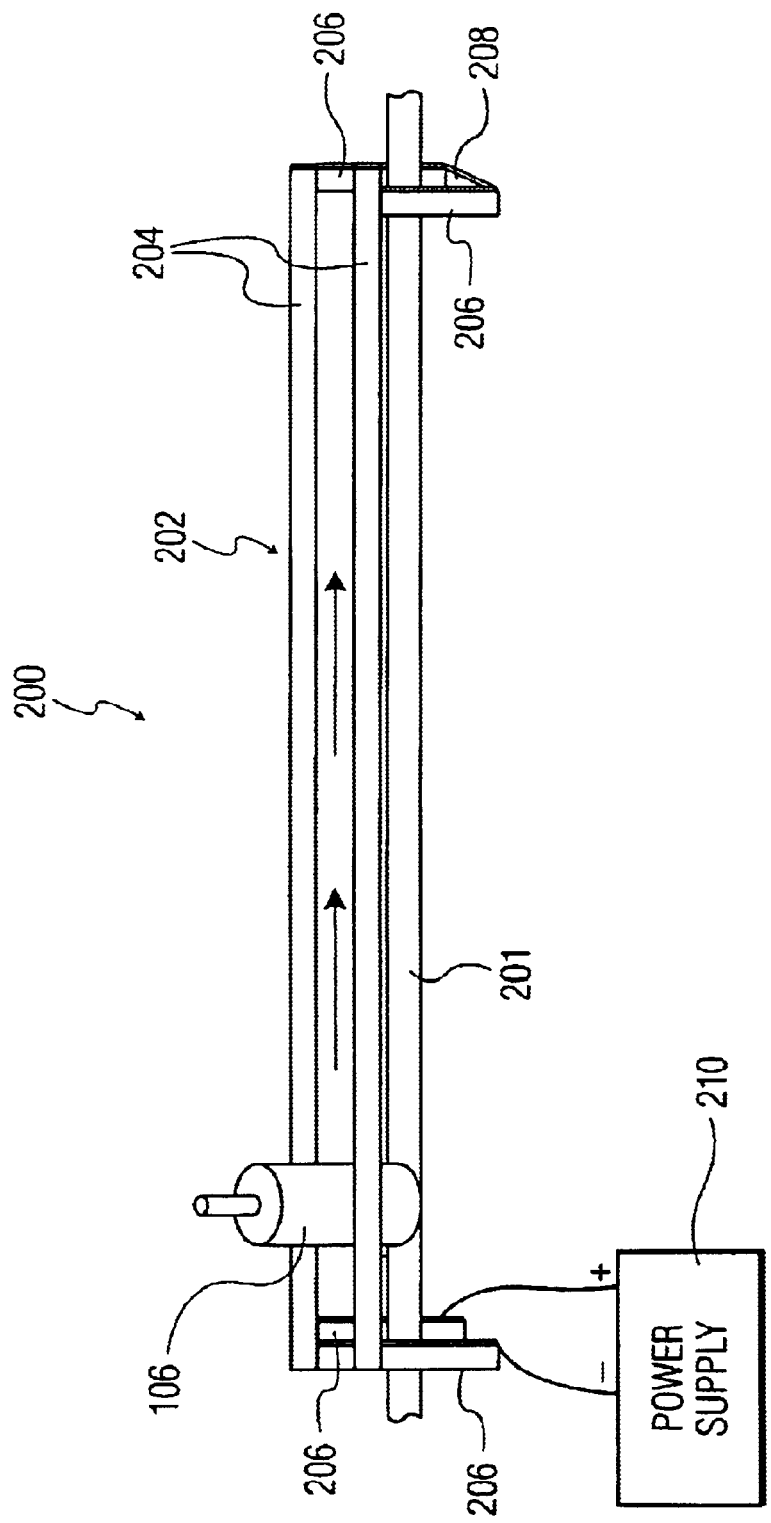
FIG. 7 is a side elevational view of an apparatus for heat testing drug canisters according to an embodiment of the invention.

Referring now to FIG. 7, an apparatus 200 for heat testing drug canisters according to the invention is shown in which a longitudinally oriented axis of the canister 106 is conveyed, for example, on a belt conveyor 201, through a heating zone of a heat induction coil 202 in a generally vertical orientation, relative to a longitudinally oriented axis of the heating zone of the induction heat coil system 202.

"Generally vertical", as used herein with respect to a canister, means a longitudinal (central) axis of the canister will be partially or fully orthogonal (perpendicular) to the longitudinally oriented axis of the heating zone of the heating assembly (e.g., induction heat coil system 202). The canister travels along, and generally parallel to, the longitudinal axis of the heating zone. It will be appreciated by a skilled artisan that the canister can be oriented at an angle between the horizontal and vertical axes so as to have a vertical component of inclination with respect to the longitudinal axis of the heating zone. The generally vertical component of the canister is about ≧45° to about 135°, relative to the longitudinal axis of the heating zone, preferably, about ≧75° to about 105°, more preferably, about 90°.

In FIG. 7, the vertically oriented longitudinal (central) axes of the valve assembly and the body of each canister 106 are the same. They are oriented in a generally vertical position (as described herein), such that the valve assembly is located (fully) outside of the heating zone formed between the parallel rails of the induction heating coil system when conveyed therethrough, while the body is located substantially between the rails of the heating zone. This embodiment should be compared to the substantially horizontal orientation of the longitudinal axis of the canister, relative to the longitudinally oriented axis of the heating zone formed within the coils of the induction heat tunnel, shown in prior art FIG. 1, in which both the valve assembly and the body of each canister 106 are located fully (or substantially) within the heating zone of the induction heating coil when conveyed therethrough.

The invention is directed to a heat stress test of canisters, preferably, an in-process heat stress test for drug canisters. The integrity of a drug canister is important because the drug contained therein is a medical therapy for a patient. An impaired canister increases the risk that the patient will not get his or her recommended dosage of medication when the impaired canister is actuated. Preferably, the drug canister is fabricated out of metal, and the heat stress is applied via an induction heat tunnel. The invention is applicable to any size of canister, as one of ordinary skill in the art can routinely design a heating zone to accommodate the shape and size of the canister, while meeting the elements of the invention.

Furthermore, other (non-drug) types of canisters can also benefit from the invention. For example, any canister containing a propellant (e.g., aerosol/pressurized cans that contain CFCs, HFAs, or the like) can benefit from heat stress testing. Thus, hair-care products, such as hair spray, and industrial products, such as cleaners and lubricants, are representative examples of non-drug applications for the invention taught herein.

Nearly all canisters, when used, contain at least one air space (void, pocket, etc.) therein. In one embodiment of the invention, the one or more air spaces present in the canister are positioned (along with the valve assembly) partially or fully outside of the heating zone of the heating assembly.

Looking at the invention shown in FIG. 7, it can be seen that transporting canisters 106 with their longitudinal (central) axes in a generally vertical orientation through a heating zone of the induction coil system 202 (relative to the longitudinally oriented central axis of the heating zone) minimizes and/or prevents most or all of the air void volume of the canisters 106 from being exposed to direct heat radiation. This is because an air space(s) will move to the top of the canister when the valve assembly and the body of the canister are held in a generally vertical position relative to the longitudinally oriented axis of a heating zone of an induction heat tunnel, that itself, is positioned parallel to the ground, where, like in most cases, air is less dense (lighter) than the density of the canister's contents.

Thus, the canister valve assembly and a portion (preferably, most) or all of the air space(s) located inside of the canister can be kept outside of the heating zone when the canister (valve assembly and body) is held in a generally vertical position as described herein. As discussed above, it was determined that in the prior art heat stress testing system of FIG. 1, where canisters 106 are conveyed through the induction heat tunnel 100 in a substantially horizontal orientation (as described herein), the valve assembly area was subjected to direct heat, which contributed to the observed failures.

In the invention shown in FIG. 7, by orienting the canister 106 (valve assembly and body) in a generally vertical orientation (as described herein), the canister body is fully exposed to the heat stress radiation being applied in the heating zone of the induction coil system 202, but the canister valve assembly and some or all of the air space(s) contained within each canister 106 are not exposed (or are briefly exposed) to the applied heat stress radiation. In other words, each canister 106 comprises upper and lower portions. The upper portion of the canister comprises the valve assembly, some or all of the air space(s) present within the canister 106 when it is held in a generally vertical orientation (as described herein), and, optionally, part of the body. The lower portion of the canister comprises most (or all) of the body. The upper portion is kept outside of the heating zone of the induction coil system 202 contemporaneously with the lower portion being heat stressed inside the heating zone of the induction coil system 202.

The position of the air space(s) depends on how large of a volume of air space(s) is present and the orientation of the canister. Thus, if the air space volume is small, it will be usually located in the proximity of the top of the canister when it is held upright. Since the valve components are also positioned at the upper portion of the canister, small air space volumes will also be kept outside of the heating zones when the canister is held in a generally vertical position (as described herein). As a result of the heating of the lower portion of each canister, resistive heat generated at the side walls of the canister dissipates readily into the (liquid) product, minimizing any localized heat treatment. This was confirmed by an x-ray image of a filled canister positioned in a generally vertical orientation (as described herein) after having been heated. This arrangement provides, in effect, for more gradual heating of the canister than is provided by the prior art system illustrated in FIG. 1. It is preferable to keep the valve assembly outside of the heating zone so that it is not directly exposed to heat radiation.

When the canister is conveyed through the heating zone, heat radiation is uniformly applied to all canister parts within the zone. Target maximum temperatures for the canister are routinely determined by a skilled artisan and depend on the type of canister being tested and the percentages and types of ingredients inside of the canister. For example, in the Proventil® studies discussed herein, an aluminum canister contains albuterol (active ingredient) and a combination of trichloromonofluoromethane and dichlorodifluoromethane (propellants). The recommended maximum storage temperature for this particular canister is 49° C./120° F.—112 psig. A preferable range for most drug and propellant containing canisters is about 56° C./133° F. to about 68° C./154° F., which equates to about 130 psig to about 160 psig.

The outside of the canister is heated until the inside contents have reached their maximum desired temperature. The duration of heat application to the canister depends on the desired temperature, the canister components and contents, and the efficacy of the heating system. Preferably, it should take less than thirty seconds of heating to reach the desired maximum temperature, at which point the canister will be conveyed outside of the heating zone. The actual temperature within the canister may be determined in any of a number of ways, as are known in the art. For instance, a temperature sensor can be attached to an inside or outside portion of the canister to give direct (inside reading) or calculated (outside reading) values. Alternatively, soon after the canister has been tested, preferably, within ten to fifteen seconds so that little to no heat has dissipated from it, the canister can be pressure tested to give an internal pressure, which can be converted into a temperature reading.

In one embodiment of the invention, the apparatus further comprises a power supply for supplying power to the heating assembly when the canister valve body is positioned substantially within the heating zone.

In another embodiment of the invention, the power supply for activating the heating assembly can be intermittent, such that (i) the power is on when the canister bodies are conveyed through the heating assembly, and (ii) the power is off when the canister valve assemblies and, optionally, any air spaces located within the canisters are conveyed through the heating assembly. This is particularly useful for highly heat sensitive (e.g., susceptible to change due to heat) valve assemblies and highly heat sensitive air spaces contained within the canisters.

In yet another embodiment of the invention, where the valve assemblies and any air space(s) located within the canisters will pass through the heating zone area, and where the valve assemblies and any air space(s) located within the canisters are not overly sensitive to heat, a power supply for the heating assembly need not be intermittent, but may be kept constant. For intermittent heating, the apparatus can be designed as described herein, with each canister body being positioned substantially inside the heating zone during heat testing, while the canister valve assembly is positioned substantially or completely outside of the heating zone during heat testing, and, optionally, any air spaces located inside the body of each canister are partially or fully positioned outside of the heating zone during heat testing. Once the target temperature has been reached in the body of each canister, the intermittent heating embodiment can shut off the heating power supply to enable the valve assembly of each canister and, optionally, any air spaces contained within each canister, to pass through a reduced temperature environment in the heating zone.

In contrast to the intermittent embodiment, a constant (heating assembly) temperature embodiment would pass the valve assemblies and any air spaces contained within the canisters through a heating zone having about the same temperature as that which heated the canister body, but for a much shorter time. For example, the canister body could be heated for about 2–10 seconds, preferably, 2–5 seconds, to the target temperature. Then, a trap door could open to let the canister pass through, causing the valve assemblies and any air space(s) contained within the canisters to also pass through the heating zone in a much shorter time, for example, about <1 second.

In another embodiment of the invention, an apparatus and a method for heat testing canisters are provided in which the valve components and, optionally, the air space(s) contained within the canisters are positioned substantially or completely outside of a heating zone when the heat is being applied, and the canisters are transported through an induction coil heating system, such that the longitudinal (central) axis of each canister is in a generally vertical orientation relative to a longitudinally oriented (central) axis of the heating zone of the induction coil heating system, and the canister travels in a direction along, and generally parallel to, the longitudinal (central) axis of the heating zone.

In another embodiment of the invention, a system is provided for heat stress testing at least one canister, the system comprising an inventive apparatus as described herein and at least one canister comprising a body and a valve assembly, wherein the system operates in the same manner as described above for the inventive apparatus.

The conveying assembly may be any known device useful for transporting items. FIG. 7 shows a belt-type of conveyor assembly. Alternatively, the canisters 106 could be held from above by a mechanical arm (not shown) of an automated conveying system and thereby transported through the induction coil 202.

While an induction heat tunnel is a preferred system for heat stressing a metal canister, other types of heating systems and other types of canisters are within the scope of the invention. Aluminum canisters are preferred for many well-known reasons, including their wide adaptability to different types of formulations inside of the canister. Other canister types will work too in the invention, for example, canisters fabricated from metal, plastic, ceramic, and the like.

Other types of heating elements that can be used include heating blocks, water baths, microwaves, infrared, laser, and the like, so long as the valve assemblies and, optionally, any air space(s) contained within the canisters, are positioned substantially or completely outside of the heating zone during the heating operation of each canister body. It is usually preferable to always keep the valve assemblies completely outside of the heating zone. All the embodiments of the invention share the common feature that they minimize or avoid completely the application of heat stress to the canister valve components and, optionally, any air space(s) contained within the canister.

Referring back to FIG. 7, the heat induction coil system 202 is, preferably, a single winding coil defined by parallel, spaced apart rails 204 mounted on legs 206, with the legs 206 at an exit end electrically connected together by a cross bar 208. In this case, the rails 204 also serve as guides for the canisters 106. A power supply 210 has a positive lead connected with one rail 204 at an entrance end and a negative lead connected with the other rail 204 at the entrance end.

Preferably, the heating assembly is formed by an induction coil system comprising a single or multiple induction heating coils, which provide a heating zone therebetween for heating canisters with electromagnetic waves. In one embodiment of the invention, the induction coil system is formed by two parallel rails comprising two ends opposite to each other for guiding the canisters in an orientation having a generally vertical component (as described herein), with the rails being electrically connected together at the one end, and being connected to positive and negative leads of a power supply, respectively, at the opposite end. In such a case, the induction coil system can be a plurality of coils (e.g., 2 or 3 coils). Alternatively, if desirable, for instance, when the space holding the canister is a limiting factor, the induction coil system may be a single winding coil, like the one shown in FIG. 7.

In another embodiment, the induction coil system is a multiple winding coil having a central axis with the generally vertical component of each canister's orientation as the canisters are moved through the induction coil system. The conveying assembly includes an arrangement for positioning each canister partially within the induction coil system, such that the valve assembly of each canister is positioned substantially or completely outside of the induction coil system. It is preferable to provide a power supply for controlling the heating assembly so as to activate a heating zone of the induction coil system only when the arrangement positions a canister partially within the induction coil system such that: (i) the canister body is positioned substantially within the heating zone, and (ii) the canister valve assembly is positioned substantially or completely outside of the heating zone. The power supply may include a negative lead connected with one end of the multiple winding coil, and a positive lead connected to an opposite end of the multiple winding coil.

Figure 8:
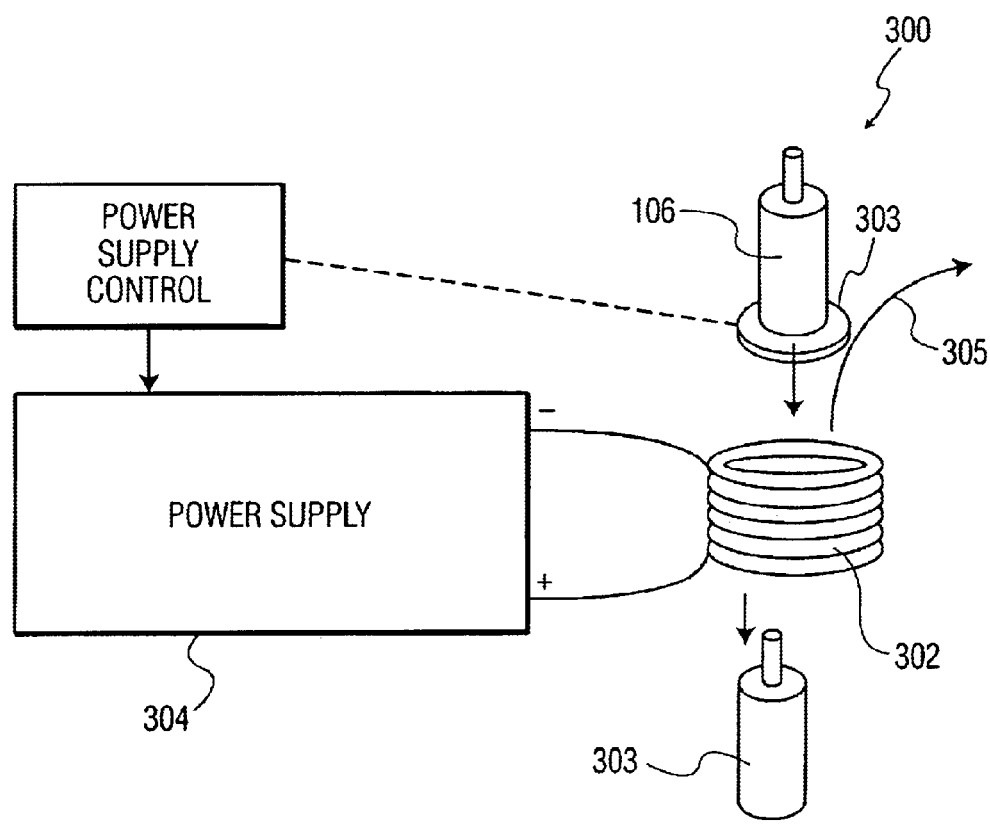
FIG. 8 is a side elevational view of an apparatus for heat testing drug canisters according to another embodiment of the invention.

A modified apparatus 300 for heat testing canisters according to the invention is shown in FIG. 8. A heat induction coil system 302 comprises a coil(s) for defining a heating zone therebetween. In an apparatus 300, the heat induction coil system 302 is provided with opposite ends, a plurality of turns or windings, a power supply 304 having a negative lead connected to one end of the induction coil system 302, and a positive lead connected to the opposite end of the induction coil system 302. In this embodiment, the canisters 106 are transported one at a time in a generally vertical orientation within the induction coil system 302 (the longitudinal axis of each canister has a generally vertical component relative to the longitudinally oriented axis of the heating zone of the induction coil system 302), such that the valve components of the canisters 106, and, optionally, part or all of any air space(s) contained therein, are positioned above and, thereby, substantially (preferably, completely) outside of the heating zone of the induction coil system 302. This type of arrangement protects the valve components from direct heat when heat radiation is applied to the rest (body) of the canister.

For example, the canisters 106 can be placed on a platform 303 that acts as a conveyor and can be lowered by lowering means, such as a piston/cylinder arrangement (not shown) or other suitable means through an induction coil system 302. After the induction coil system 302 is energized to heat the main body of each canister 106 (e.g., the portion below the valve components), the power to the induction coil system 302 is terminated, and the heated canister 106 is dropped through the induction coil system 302 so as to exit through a lower end thereof. This can occur by any suitable means, such as a trap door opening in a platform 303, tilting of the platform 303 after it passes through the induction coil system 302, and the like. Alternatively, the canisters 106 can be held by a mechanical arm (not shown) and removed from the upper end of coil 302 in the direction of arrow 305.

The apparatus of FIG. 8 differs from that of FIG. 7 in that the canisters 106 are stationary when they are heated within the electromagnetic heating zone of the induction heating coil system 302 shown in FIG. 8, while the canisters 106 shown in FIG. 7 remain in motion when they are being heated within the induction coil system 202. One of ordinary skill in the art can modify either apparatus to provide for stationary or moving canisters as desired.

In another embodiment of the invention, the arrangement permits the entire canister, including all of its components, to pass through and out of the induction coil system. Arranging the apparatus in this manner makes it adaptable to permit a canister to pass entirely through and out of an induction coil (e.g., the heating zone) that operates continuously, semi-continuously or discontinuously.

A continuous method is one in which the heating environment is kept at a steady state. Continuous methods can be advantageous in a number of situations, for instance, where it has been determined that the integrity of the valve assembly of the canister will not be destroyed or impermissibly compromised (e.g., unsafe to use) if it (briefly) passes through the heating zone. In continuous heating systems, the canister body can be heated for a number of seconds to reach a desired temperature, then the canister is ejected such that the valve assembly and, preferably, any air space(s) contained within the canister, quickly pass through the heating zone. In such situations, an embodiment of the invention may be arranged to let the canister valve assemblies pass through the heating zone. Conversely, if the canister valve assemblies are heat sensitive, it would be advantageous to keep them substantially (preferably, completely) outside of the heating zone as discussed in detail herein.

Semi-continuous and discontinuous processes can reduce and/or shut off the heat in the heating zone for a period of time during the testing. These types of processes are particularly advantageous when both the body and valve of the canister pass through the heating zone. Thus, if the valve assembly, canister contents and/or air space(s) positioned within the canister are particularly heat sensitive, a skilled artisan could choose a semi-continuous or discontinuous method, that is, a method that turns the heating assembly on and off depending on where the canister body and canister valve assembly are located and how long they have been there. For example, the heating assembly can be turned on when the canister valve assembly is positioned substantially or completely outside of the heating zone, and turned off when the canister valve is located partially or fully inside of the heating zone. In many situations, a semi-continuous method works well, for example, one where the canister body and canister valve assembly pass within the induction coil system during heating for one or more seconds before dropping out or moving on. A discontinuous method would turn off the heat for more than about a couple of seconds.

It is preferable that the conveying assembly conveys each canister in a specific orientation through the induction coil system (e.g., generally vertical as described herein), which permits part of the canister to be outside of the heating zone of the induction coil system (e.g., the canister valve assembly and any air spaces contained within the canister).

In accordance with these preferred aspects of the invention, a method is taught for heat (stress) testing canisters having bodies and valve assemblies, and, optionally, having one or more air spaces contained therein, the method comprising the steps of:

(a) conveying the canisters in an orientation (e.g., one that is generally vertical as described herein) that positions them partially within a heating zone of a heating assembly, such that the valve assemblies and, optionally, the one or more air spaces, are positioned substantially or completely outside of the heating zone;

(b) supplying power to the heating assembly when the canisters are partially positioned within the heating zone so as to heat the bodies of the canisters;

(c) optionally, stopping the supply of power to the heating assembly after a predetermined amount of time; and (d) removing the canisters from within the heating zone of the heating assembly.

It is preferable for the canisters to be guided in an orientation having a vertical component (longitudinal axis of each canister is generally vertical relative to the longitudinally oriented axis of the heating zone of the induction coil heating system) by means of rails when the canisters are conveyed by a conveying assembly. In another embodiment of the invention, each canister is positioned partially within an induction coil system by a conveying arrangement, such that the canister body is positioned substantially inside a heating zone of the induction coil system, while at the same time, the canister valve assembly and, optionally, any air space(s) contained within the canister, are positioned substantially or, preferably, completely outside of the induction coil system's heating zone, and power is supplied to the induction coil system only when the canister is in this partial position.

Other than in the operating examples or where is otherwise indicated, all numbers used in the specification and claims expressing quantities of ingredients, reaction conditions, and so forth, are understood as being modified in all instances by the term "about." Furthermore, temperature-pressure relationships described herein are for Proventil® inhalation aerosol canisters. Temperature-pressure relationships for other types of formulations (e.g., different active ingredients and/or propellants and/or percentages of ingredients) can be routinely determined by one of ordinary skill in the art.

EXAMPLE 1

Figure 1:
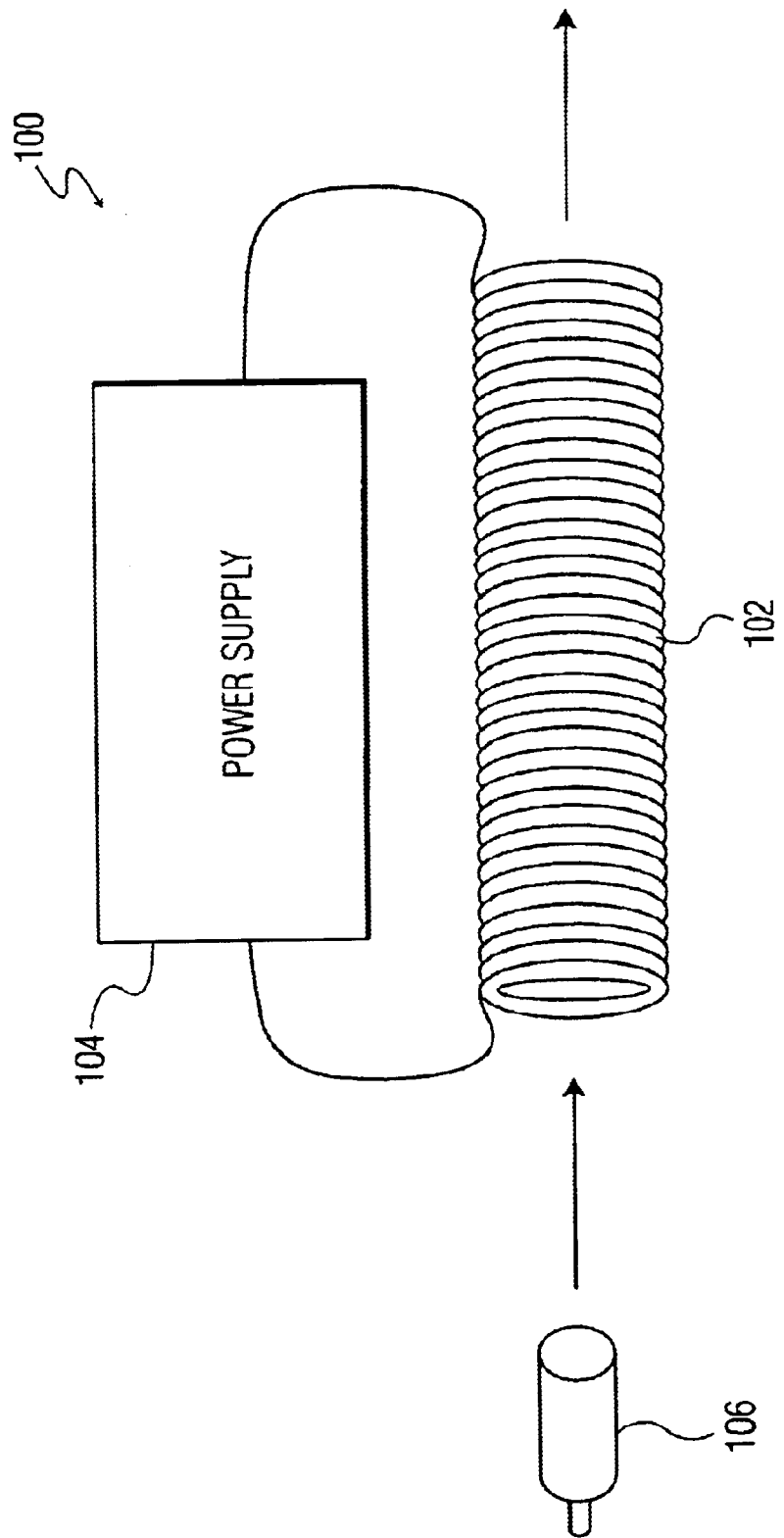
FIG. 1 is a side elevational view of an induction heat tunnel for heat testing canisters according to the prior art.
Figure 2:
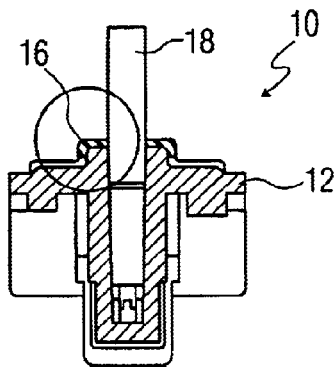
FIG. 2 is a partial cross-section of a side elevational view of a typical, normally functional valve.
Figure 3:
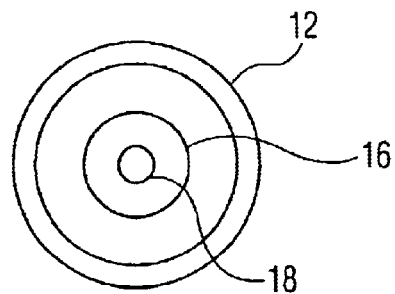
FIG. 3 being a top plan view thereof.
Figure 4:
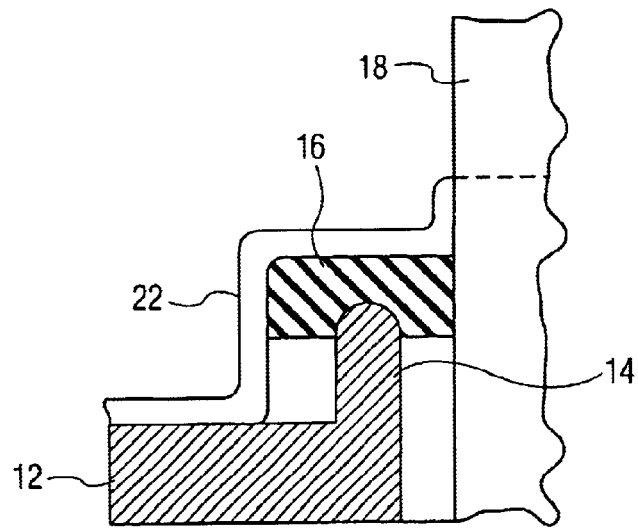
FIG. 4 is an enlarged cross-sectional view of the circled portion of the valve of FIG. 2.
Figure 5:
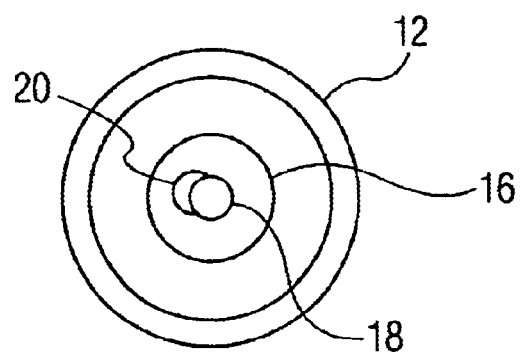
FIG. 5 being a top plan view of a valve similar to the valve of FIG. 1 with a deformation therein.
Figure 6:
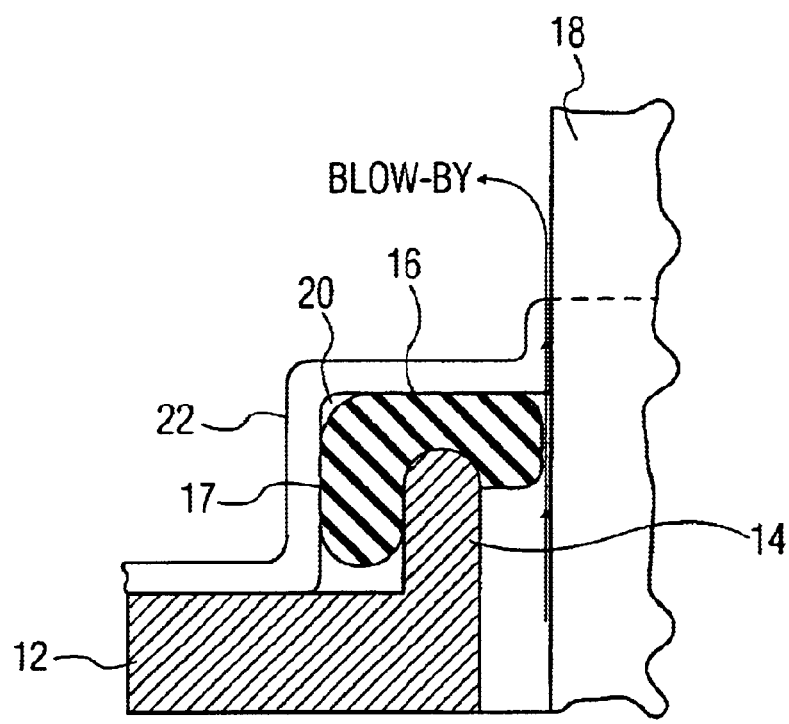
FIG. 6 is an enlarged cross-sectional view of the circled portion of the valve of FIG. 2, with the deformation therein.

The valve seats of canisters can be damaged when exposed to conventional heat stress testing equipment, like that shown in FIG. 1, with an induction heat tunnel in which canister valve components are positioned entirely inside of a heated test area, and the canisters are transported with their longitudinal axes being in a substantially horizontal orientation through an induction coil, relative to the longitudinally oriented axis of the heating zone of the induction coil heating system. For example, conventional testing was performed on Proventil® (albuterol) Inhalation Aerosols, where the integrity of the aerosol canisters were evaluated via x-ray imaging and actuation of the valve assembly (to put the canister into mechanical action or motion, for example, pressing down a canister valve stem to release the propellants and other contents of the canister).

In the forthcoming tables reporting the results of the Proventil® studies, the following definitions apply:

"Typical" is a working functional valve that exhibits no objective evidence of a formation of a 'gap' (defined below).

"Gap" is a deformation in the valve seat that is observed under x-ray imaging analysis. Based on a visual observation, the 'gap' can be categorized by degree—'very slight gap,' 'slight gap' and 'gap.' The demarcations between these three degrees are not absolute and depend on the application of the canister. A gap can be so large that the valve seat can separate from the valve body. Only the 'gap' category of deformation has been observed to potentially cause "blow-by."

"Other Observations" in the 'x-ray image' and 'actuation' columns of the tables note any other evidence (e.g., defects) that the integrity of the canister may have been affected, such as, the separation of the valve seat from the valve body, base inversion (a condition where a convex portion of the canister base 'pops' and relieves the internal pressure within the canister), doming of the valve (shape deformation), long bursts of drug product spraying (discharging), continuous spraying (discharging) of drug product, and empty canisters due to heat stress deformation of the valve seat.

The components used in the Proventil® studies include the following:

induction heater (Lepel Corp., Edgewood, N.Y.): a 3-inch copper coil and a 7.5 kW DC power supply, which are configured to heat and carry through canisters having their longitudinal axes oriented in a generally vertical position with respect to a longitudinally oriented axis of a heating zone of the induction coil heating system;

16 ml aluminum aerosol canister;

aerosol valve multi-part assembly; and each canister has a neck finish for an internal gasket and a pressure fill valve, the sizes/dimensions being:

| Canister Sizes/Dimensions | |
| --- | --- |
| *Overall Height: | 2.315"–2.335" |
| *Body Outside Diameter: | 0.870"–0.874" |
| *Neck Outside Diameter: | 0.782"–0.790" |
| *Neck Groove Diameter: | 0.665"–0.675" |
| Neck Flange Thickness: | 0.176"–0.184" |
| *Neck Internal Diameter: | 0.650"–0.660" |
| Overflow capacity: | 12.5 mL minimum |
| Wall thickness: | 0.014"–0.018" |
| Weight: | 5.0 g–5.1 g |
| Canister Body Material: | aluminum. |
| Canister Valve Sizes/Dimensions | |
| *Ferrule Skirt Length: | 0.360"–0.370" |
| *Ferrule Inside Diameter: | 0.795"–0.805" |
| *Stem (Core) Top Outside Diameter: | 0.124"–0.126" |
| Canister Valve Materials: | stainless steel, nitrile (Buna-N) rubber, aluminum and plastic. |
| Canister Valve Components: | ferrule, seat, stem (core), spring, flap, cup (body), dip cup, radius plug and gasket. |

*Measured at Incoming Receival

In the Proventil® tests, lagered and unlagered canisters were heat stressed to internal pressures ranging from 80–90 psig to 135–145 psig using a conventional induction heat tunnel 100 and a conventional method of heat stress testing canisters—horizontal entry of entire canisters (as described herein) through the heating zone of the induction heat tunnel. Lagering is defined herein as a process of holding canisters in an inverted position (valve facing downwards) for a period of time to allow the valve components to come to equilibrium with the formulation. Unlagered canisters are 'fresh' product.

The canisters were lagered for no less than 28 days to ensure equilibrium within the canister has occurred. Previous studies have suggested that induction heat stressing of lagered canisters produced higher incidences of valve seat deformation. Thus, the use of lagered canisters may increase the rate of valve seat deformation and exemplify the mode of failure.

TABLE I

| Internal Pressure Target Range | X-Ray Image | | | | | Actuation | | | |
| --- | --- | --- | --- | --- | --- | --- | --- | --- | --- |
| | Typical | Gap | Slight Gap | Very Slight Gap | Other Observations | Typical | Blow-By | Other Observations or Not Actuated | Comments |
| 80–90 | 11 | 2 | 3 | 4 | 0 | 19 | 1 | 0 | n = 20 lagered |
| 80–90 | 11 | 0 | 4 | 5 | 0 | 20 | 0 | 0 | n = 20 unlagered |
| 110–120 | 2 | 7 | 1 | 1 | 2 | 6 | 3 | 4 | n = 13 lagered |
| 110–120 | 1 | 7 | 0 | 1 | 2 | 3 | 4 | 4 | n = 11 unlagered |
| 135–145 | 1 | 9 | 1 | 1 | 9 | 5 | 6 | 10 | n = 21 lagered |
| 135–145 | 2 | 11 | 1 | 0 | 6 | 6 | 7 | 7 | n = 20 unlagered |

As shown in Table I, twenty lagered and twenty unlagered canisters 106 were thermally stressed to 80–90 psig (34–39° C.). The canisters 106 showed no visible signs of damage (to the naked eye) when they were passed through the induction heat coil 102 in a horizontal orientation (as described herein). The canisters 106 were then evaluated by x-ray imaging and valve assembly actuation analysis (e.g., presence or absence of "blow-by") for rubber valve seat deformations. Examining the canisters after the testing was completed, it was determined that two of the twenty lagered canisters 106 developed gaps, as per the following Table I. One of the two canisters with gaps exhibited blow-by during actuation of the valve assembly. None of the unlagered cans thermally stressed at 80–90 psig showed gaps in the x-ray imaging analysis or exhibited blow-by during actuation of the valve assembly.

Increasing the canister pressure to 110–120 psig (48–52° C.) in the induction heat tunnel often resulted in destroying the integrity of the canister, as evidenced by leakage of product from the stem of the valve assembly or by base inversion of the canisters after the canisters have exited the induction heating coil. This was noted for both lagered and unlagered canisters.

The results tabulated in Table I indicate that induction heating of the canisters 106 in a conventional position (horizontal entry of entire canisters through the heating zone of the induction heat tunnel, such that the longitudinal axes of the canisters are oriented horizontally relative to the longitudinal axis of the heating zone) was damaging the valve assembly and/or other components of the canister. Many of the valve assemblies could not be actuated during the testing for "blow-by" because the drug product had already been released (discharged) when the valve assembly was damaged.

The number of canisters that exhibited canister base inversion increased when the canisters 106 were stressed to 135–145 psig, as shown in Table I. The canisters that survived the heat stress of 135–145 psig were analyzed by x-ray imaging and tested for blow-by during actuation of the valve assembly. The results in Table I show a number of canisters having large gap deformations in the valve seat area. In addition, a majority of the canisters 106 with gaps also exhibited blow-by during actuation of the valve assemblies.

Further, a temperature mapping of the outside surface of the canister was conducted using the induction heating tunnel 100. Temperature sensitive paints that melt at 73° C., 79° C., 87° C., 93° C., 107° C. and 121° C. (163° F., 175° F., 188° F., 200° F., 225° F. and 250° F.) were applied to a surface of the canister from the upper portion of the canister (including, the valve assembly) to the bottom of the canister to determine the effects of induction heating on the outside surface temperature of the canister. Table II shows the results of these surface temperature distribution studies The temperature sensitive paint liquefies or melts and then turns clear when the substrate is at a temperature at or above the indicated temperature. The terms "MELTED" or "NOT MELTED" denote these observations. The term "NOT USED" denotes that the temperature paint was not applied to the canisters. The data indicates that the "top" side (upper portion) of a canister, positioned with its longitudinal axis horizontally oriented relative to the longitudinally oriented axis of the heating zone of the induction coil heating system, was at a higher temperature than the "bottom" side (lower portion) of the canister. For canisters heated to internal pressures of 80–90 psig, temperatures between 87–93° C. (188–200° F.) were observed on the "top" side of the canisters. The same results were obtained for the valve area. The results also indicate that the "bottom" side of the canisters reached temperatures of 73–79° C. (163–175° F.). When the canisters were heated to yield an internal pressure of 120 psig, canister surface temperatures of above 107° C. (225° F.) in the valve area were observed.

The results of Table II offer a plausible explanation as to why a canister that was conveyed horizontally (as described herein) through a heat induction tunnel might fail—there is a lack of fluid present in the canister valve stem area, which results in a localized heating of the valve area due to reduced (e.g., minimal) heat dissipation. An x-ray image of the canister in the substantially horizontal position (as described herein), verified this by showing that the valve area was free of drug product (fluid). The lack of fluid in that area could provide localized heat spots in the valve seat.

EXAMPLE 2

Experiments were conducted to determine the effect of induction heating the canisters 106 in a generally vertical orientation (as described herein) with the modified apparatus of FIG. 8. In one experiment, different sections of the canisters 106 (bottom, mid-section and valve area) were heated in the generally vertical orientation (as described herein). All canisters were pre-cooled to 15° C. prior to being heated in the induction coil system 302. This was done to simulate a production environment, where a chilled (0–4.4° C.) product is filled at a filling room temperature of 17–23° C., and the product temperature is expected to be approximately 15° C. when the canisters 106 reach the heat stress test apparatus.

Figure 9:
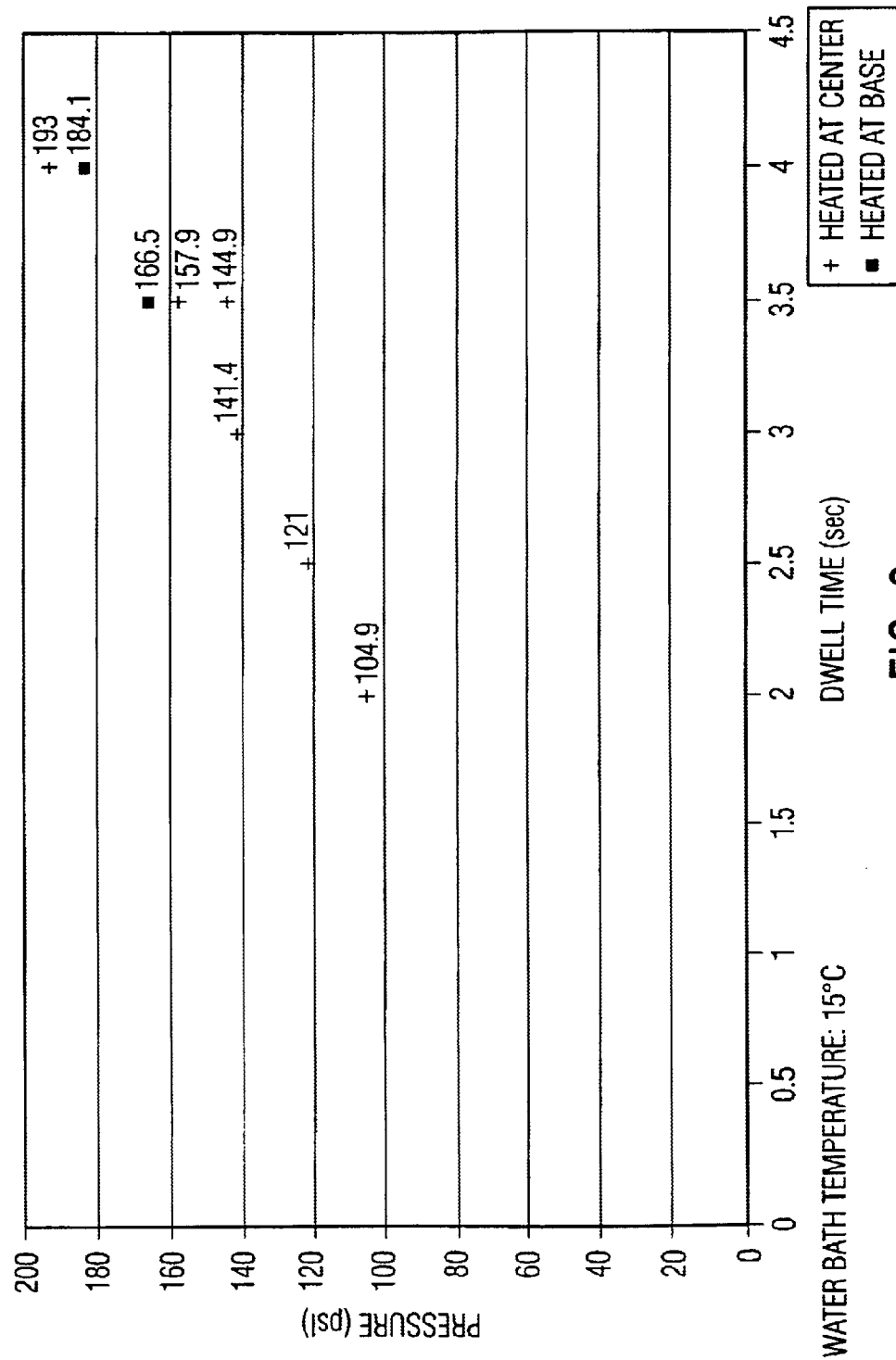
FIG. 9 is a graphical diagram of pressure as a function of dwell time for canisters heated according to methods of the invention.

Results from this experiment, shown in FIG. 9 (graphical diagram of pressure as a function of dwell time for heated canisters according to the invention), indicate that the pressure/dwell time data is comparable for canisters heated in the middle (center) and bottom portions of the canister. Application of heat stress to these sections of the canister did not produce deformation in the rubber valve seat and exhibited no blow-by during actuation of the valve assembly, as shown in Table III.

TABLE II

| Pressure Range (psi) | Section of the Canister | Paint Melting Temperature (° C./° F.) | | | | | | Surface Temperature Observed |
|---|---|---|---|---|---|---|---|---|
| | | 73/163 | 79/175 | 87/188 | 93/200 | 107/225 | 121/250 | |
| 80–90 | Valve | Melted | Melted | Melted | Not Melted | Not Melted | Not Melted | 87–93° C. (188–200° F.) |
| 80–90 | Side (Top) | Not Used | Melted | Melted | Not Melted | Not Melted | Not Melted | 87–93° C. (188–200° F.) |
| 80–90 | Side (Bottom) | Melted | Not Melted | Not Melted | Not Melted | Not Melted | Not Melted | 73–79° C. (163–175° F.) |
| ~120 | Valve | Not Used | Not Used | Not Used | Not Used | Melted | Not Melted | 107–121° C. (225–250° F.) |

TABLE III

| Canister Portion Stressed | Pressure (psig) | Number of Cans Stressed | X-Ray | | | | Actuation | |
|---|---|---|---|---|---|---|---|---|
| | | | Typical | Gap | Slight Gap | Very Slight Gap | Typical | Blow-By |
| Valve | 97 | 5 | 3 | 1 | 1 | 0 | 4 | 1 |
| Middle | 121 | 20 | 20 | 0 | 0 | 0 | 20 | 0 |
| Base | 167 | 5 | 5 | 0 | 0 | 0 | 5 | 0 |

As can be seen in Table III, when five canisters were heated directly in the valve areas to an internal pressure of approximately 97 psig, canisters having 1 "gap", 1 "slight gap" and 1 "blow-by" were found. Attempts to heat stress canisters in the valve area to internal pressures greater than 97 psig resulted in canister base inversion and/or leakage of product from the valve stem. These results indicate that stress heating canisters in the valve area in the generally vertical position (as described herein), where only propellant vapor is in contact with the canister surface, resulted in failures when stressed to an internal pressure of greater than approximately 100 psig.

Further, the outside surface temperatures of the canisters 106 that were heated with a static induction coil system 302 in a generally vertical orientation (as described herein) were assessed using temperature sensitive paints, as discussed in detail above. The study procedure was similar to that described previously in relation to Table II. The data from this study is presented in Table IV.

TABLE IV

| Pressure Range (psi) | Section of the Canister | Paint Temperature (° C./° F.) | | | | | | Surface Temperature Observed |
|---|---|---|---|---|---|---|---|---|
| | | 52/125 | 66/150 | 79/175 | 87/188 | 93/200 | 107/225 | |
| ~150 | Top | Melted | Melted | Not Melted | Not Melted | Not Melted | Not Melted | 66–79° C. (150–175° F.) |
| ~150 | Middle | Melted | Melted | Melted | Melted | Not Melted | Not Melted | 87–93° C. (188–200° F.) |
| ~200 | Top | Not Used | Melted | Melted | Not Melted | Not Melted | Not Used | 79–87° C. (175–188° F.) |
| ~200 | Bottom | Not Used | Melted | Melted | Melted | Not Melted | Not Used | 87–93° C. (188–200° F.) |

The results indicate that canisters stressed up to 200 psig, by heating generally vertically oriented canisters (as described herein) in the mid-section of the canister body, reached temperatures of 79–87° C. around the valve area. The highest surface temperatures recorded in this orientation were 87–93° C. at the bottom region of the canister, which was exposed to direct heat radiation. These results can be contrasted to the surface temperatures recorded for canisters oriented in a substantially horizontal position (as described herein), where stress internal pressures of only 120 psig resulted in valve area temperatures of 107–121° C. As stated previously, a plausible explanation is that heat transfer/dissipation is not as efficient in the gaseous state, producing localized hot spots and generating much higher transient pressure when areas containing vapor phase are subjected to direct heat. Excessive heating of the valve area would explain the occurrence of valve rubber seat deformation when the canister was heat stressed in a substantially horizontal position (as described herein), and the valve region was exposed to direct heat radiation from the induction coil system with the canister positioned in a generally vertical position (e.g., valve-up, as described herein).

The results of these studies suggest that the substantially horizontal position or orientation of the canisters 106 (as described herein) in the prior art induction heat tunnel 100 shown in FIG. 1 may cause valve rubber seat deformation and blow-by during actuation of the valve assembly. In contrast, the inventive induction heat tunnel described herein can transport canisters in a generally vertical position or orientation (as described herein), and utilize the appropriate induction coil placement to avoid direct heat stressing in the valve area, which makes it useful for stress testing canisters without causing rubber seat valve deformation and blow-by during actuation of the valve assembly.

The above description is not intended to detail all modifications and variations of the invention. It will be appreciated by those skilled in the art that changes can be made to the embodiments described above without departing from the inventive concept. It is understood, therefore, that the invention is not limited to the particular embodiments and examples described above, but is intended to cover modifications that are within the spirit and scope of the invention, as defined by the language of the following claims.

What is claimed is:

1. An apparatus for heat testing a canister comprising a body and a valve assembly, the apparatus comprising:
 (a) a heating assembly comprising a heating zone for heating at least a portion of the canister; and
 (b) a conveying assembly for conveying the canister in an orientation that positions the canister partially within the heating zone during the heat testing, such that:
  (i) the body is positioned substantially inside of the heating zone; and
  (ii) the valve assembly is positioned substantially or completely outside of the heating zone.

2. The apparatus according to claim 1, wherein the canister has one or more air spaces contained therein, which are positioned partially or fully outside of the heating zone during the heat testing.

3. The apparatus according to claim 1, further comprising:
 (c) a power supply for supplying power to the heating assembly.

4. The apparatus according to claim 1, wherein the heating zone is heated when the body is positioned substantially therein.

5. The apparatus according to claim 1, wherein the valve assembly is positioned completely outside of the heating zone.

6. The apparatus according to claim 1, wherein the heating assembly comprises an induction coil system.

7. The apparatus according to claim 6, wherein the induction coil system comprises two parallel rails comprising two ends opposite to each other for guiding the canister in the orientation, with the rails being electrically connected together at the one end and being connected to positive and negative leads of a power supply for supplying power to the heating assembly, respectively, at the opposite end.

8. The apparatus according to claim 6, wherein the induction coil system comprises a single winding induction coil.

9. The apparatus according to claim 6, wherein the induction coil system comprises a plurality of induction coils.

10. The apparatus according to claim 6, wherein:
 the orientation of a longitudinal axis of the canister comprises a generally vertical component relative to a longitudinal axis of the heating zone, the canister travels in a direction along the longitudinal axis of the heating zone, and the induction coil system comprises at least one coil, which is a single coil or a plurality of winding coils, and has a central axis with the generally vertical component.

11. The apparatus according to claim 6, further comprising:
(a) a power supply for supplying power to the heating zone only when the body is positioned substantially inside of the heating zone and the valve assembly is positioned substantially or completely outside of the heating zone.

12. The apparatus according to claim 6, wherein the canister passes entirely through and out of the induction coil system, and the heating assembly is off for at least part of the time that the valve assembly passes through the heating zone.

13. The apparatus according to claim 1, wherein after the heating zone has been heated, it is maintained at a constant temperature.

14. The apparatus according to claim 1, wherein the conveying assembly conveys the canister out of the heating zone after the body has reached a desired temperature.

15. The apparatus according to claim 14, wherein after the body has reached the desired temperature, the canister is conveyed out of the heating zone, such that:
(i) the valve assembly remains positioned substantially or completely outside of the heating zone; or
(ii) the valve assembly passes through at least a portion of the heating zone.

16. The apparatus according to claim 14, wherein the heating zone is maintained at a first temperature for heating the body to the desired temperature, and after the body has reached the desired temperature, the canister is conveyed out of the heating zone, such that:
(i) the valve assembly remains positioned substantially or completely outside of the heating zone; or
(ii) the valve assembly passes through at least a portion of the heating zone while it is being maintained at a second temperature that is lower than the first temperature.

17. The apparatus according to claim 1, wherein the conveying assembly conveys the canisters through the heating zone, such that a longitudinal axis of the canister has a generally vertical component relative to a longitudinal axis of the heating zone, and the canister travels in a direction along the longitudinal axis of the heating zone.

18. The apparatus according to claim 1, wherein the body comprises a metal.

19. The apparatus according to claim 1, wherein the canister contains a pharmaceutical drug.

20. An apparatus for heat testing a canister comprising a body and a valve assembly, the apparatus comprising:
(a) an induction heating coil system comprising a heating zone for heating at least a portion of the canister; and
(b) a conveying assembly for conveying the canister in an orientation that positions the canister partially within the heating zone during the heat testing, such that:
(i) the body is positioned substantially inside of the heating zone; and
(ii) the valve assembly is positioned substantially or completely outside of the heating zone.

21. The apparatus according to claim 20, wherein the canister has one or more air spaces contained therein, which are positioned partially or fully outside of the heating zone during the heat testing.

22. A method for heat stress testing a canister comprising a body and a valve assembly, the method comprising:
conveying the canister in an orientation so as to be positioned partially within a heating zone of a heating assembly, the conveying step comprising:
(i) positioning the body substantially inside of the heating zone; and
(ii) positioning the valve assembly substantially or completely outside of the heating zone; and
(a) heating the body to a desired temperature when it is positioned substantially inside of the heating zone.

23. The method according to claim 22, wherein the orientation of the canister is such that a longitudinal axis of the canister has a generally vertical component relative to a longitudinal axis of the heating zone, and the canister travels in a direction along the longitudinal axis of the heating zone.

24. The method according to claim 22, wherein the canister has one or more air spaces contained therein, which are positioned partially or fully outside of the heating zone when the body is being heated.

25. The method according to claim 22, wherein the heating assembly comprises an induction coil system.

26. The method according to claim 25, wherein:
the induction coil system comprises two parallel rails comprising two ends opposite to each other for guiding the canister in the orientation, with the rails being electrically connected together at the one end, and connected to positive and negative leads of a power supply, respectively, at the opposite end, and the conveying step further comprising:
(iii) guiding the canister by means of the rails.

27. The method according to claim 25, wherein:
the orientation of a longitudinal axis of the canister comprises a generally vertical component relative to a longitudinal axis of the heating zone, the canister travels in a direction along the longitudinal axis of the heating zone, and
the induction coil system comprises at least one coil, which is a single coil or a plurality of winding coils, and has a central axis with the vertical component.

28. The method according to claim 22, further comprising:
(b) conveying the canister out of the heating zone after the body has reached the desired temperature.

29. The method according to claim 22, wherein the heating zone is maintained at a constant temperature after the desired temperature of the body has been reached, and the canister is conveyed out of the heating zone, such that:
(i) the valve assembly remains positioned substantially or completely outside of the heating zone; or
(ii) the valve assembly passes through at least a portion of the heating zone.

30. The method according to claim 22, wherein the heating zone is maintained at a first temperature for heating the body to the desired temperature, and the canister is conveyed out of the heating zone, such that:
(i) the valve assembly remains positioned substantially or completely outside of the heating zone; or
(ii) the valve assembly passes through at least a portion of the heating zone while it is being maintained at a second temperature that is lower than the first temperature.

31. The method according to claim 22, further comprising:
(c) supplying power to the heating zone so as to heat the heating zone only when the body is positioned substantially inside the heating zone, and the valve assembly is positioned substantially or completely outside of the heating zone.

32. The method according to claim 22, wherein the canister passes entirely through and out of the heating zone, and the heating assembly is off for at least part of the time that the valve assembly passes through the heating zone.

33. The method according to claim 22, wherein the conveying assembly conveys the canister through the heating zone in an orientation such that a longitudinal axis of the canister has a generally vertical component relative to a longitudinal axis of the heating zone, and the canister travels in a direction along the longitudinal axis of the heating zone.

34. The method according to claim 22, wherein the valve assembly is positioned completely outside of the heating zone.

35. The method according to claim 22, wherein the body comprises a metal.

36. The method according to claim 22, wherein the canister contains a pharmaceutical drug.

37. A method for heat stress testing a canister comprising a body and a valve assembly, and, optionally, having one or more air spaces contained therein, the method comprising:
(a) conveying the canister in an orientation so as to be positioned partially within a heating zone of an induction heating coil system, the conveying step comprising:
(i) positioning the body substantially inside of the heating zone;
(ii) positioning the valve assembly substantially or completely outside of the heating zone; and
(iii) optionally, positioning the one or more air spaces, when present, partially or fully outside of the heating zone; and
(ii) heating the body to a desired temperature when it is positioned substantially inside of the heating zone.

38. A canister tested for heat stress by the method of claim 37.

39. The canister of claim 38, that comprises a pharmaceutical drug.

40. A canister tested for heat stress by the method of claim 36.

41. A canister tested for heat stress by the method of claim 22.

* * * * *